United States Patent

Holla et al.

[11] Patent Number: 5,861,304
[45] Date of Patent: Jan. 19, 1999

[54] PROCESS FOR THE ENZYMATIC SEPARATION OF ENANTIOMERS OF RAC-2-OXOTRICYCLO[2.2.1.0 3,5] HEPTANE-7-CARBOXYLIC ACID AND OF RAC-2-OXOTRICYCLO[2.2.1.0 3,5] HEPTANE-7-CARBOXYLIC ESTERS

[75] Inventors: Wolfgang Holla, Kriftel; Gerhard Beck, Frankfurt, both of Germany

[73] Assignee: Hoechst Aktiengesellschaft, Frankfurt am Main, Germany

[21] Appl. No.: 932,933

[22] Filed: Sep. 17, 1997

Related U.S. Application Data

[63] Continuation of Ser. No. 538,281, Oct. 2, 1995, abandoned.

[30] Foreign Application Priority Data

Oct. 4, 1994 [DE] Germany .......................... 44 35 242.5

[51] Int. Cl.[6] .................................................. C12P 41/00
[52] U.S. Cl. ............................................ 435/280; 435/921
[58] Field of Search ..................................... 435/280, 921

[56] References Cited

U.S. PATENT DOCUMENTS 5,248,609  9/1993  Petzoldt et al. ......................... 435/280
5,270,206  12/1993  Saccomano ............................. 435/280

FOREIGN PATENT DOCUMENTS

88/03570  5/1988  WIPO .

OTHER PUBLICATIONS

Bindra et al., "New Extensions of the Bicyclo[2.2.1]heptane Route to Prostaglandins", Journal of the American Chemical Society, 95(22) : 7522–7523 (1973).

Cervinka et al., "Absolute Configuration of (1R,2S,4R,6S,7R)–(+)–3–Oxotricyclo[2,2,1,0$^{2,6}$]heptane–7–carboxylic Acid", Collection Czechoslovak Chemical Commun., 48:3565–3566 (1983).

Bartmann et al., "Synthese eines biologisch aktiven Analogons des Prostaglandins E$_2$ (Racemat und reine Enantiomere)", Liebigs Ann. Chem., pp. 321–326 (1987).

Höfle et al., "4–Dialkylaminopyridine als hochwirksame Acylierungskataly–satoren[1,2]", Ange. Chem. 90:602–615 (1978).

Geckeler et al., "Synthese von Aminoäure–alkenylestern", Chem. Ber., 107:1271–1274 (1974).

Haslam, "Recent Developments in Methods for the Esterification and Protection of the Carboxyl Group", Tetrahedron Report, 36(93) :2409–2433 (1980).

Stanek et al., 110:231177u, abstract of CS 240,862 (1988).

*Primary Examiner*—Sandra E. Saucier
*Attorney, Agent, or Firm*—Finnegan, Henderson, Farabow, Garrett & Dunner, L.L.P.

[57] ABSTRACT

Process for the resolution of rac-2-oxotricyclo[2.2.1.0$^{3,5}$] heptane-7-carboxylic acid esters using lipase from candida.

Compounds of the formula I

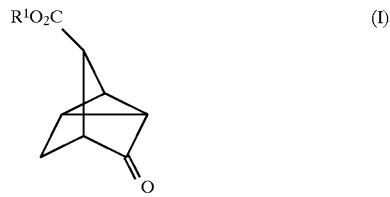

in which $R^1$ has the meanings mentioned, may be obtained in isomerically pure form from enantiomer mixtures or racemic mixtures by reacting the compound of the formula I in the presence of a lipase or esterase from porcine liver, porcine pancreas, bovine pancreas or from microorganisms such as Candida, Pseudomonas, Mucor, Rhizopus and Aspergillus, or proteases from Bacillus in the presence of water and, if desired, a cosolvent and separating from one another the esters and acids present in the solution obtained.

18 Claims, No Drawings

PROCESS FOR THE ENZYMATIC SEPARATION OF ENANTIOMERS OF RAC-2-OXOTRICYCLO[2.2.1.0 3,5] HEPTANE-7-CARBOXYLIC ACID AND OF RAC-2-OXOTRICYCLO[2.2.1.0 3,5] HEPTANE-7-CARBOXYLIC ESTERS

This application is a continuation, of application Ser. No. 08/538,281, filed Oct. 2, 1995, now abandoned.

FIELD OF INVENTION

The invention relates to a process for the preparation of optically pure compounds of Formula I, described below, by stereodifferentiating reactions of enantiomeric mixtures with the aid of a lipase, esterase or protease.

BACKGROUND OF THE INVENTION

Rac-2-Oxotricyclo[2.2.1.0$^{3,5}$]heptane-7-carboxylic acid is accessible starting from norbornadiene by the Prins reaction and a subsequent Jones oxidation, and is an important precursor for the preparation of prostaglandins (Bindra, Grodski, Schaaf, Coney, J. Am. Chem. Soc. 1973, 95, 7522; Cervinka, Habartova, Coll. Czech. Chem. Comm. 1983, 48, 3565; Bartmann, Beck, Jähne, Lerch, Wess, Liebigs Ann. Chem. 1987, 321; CS 240,862).

It has been known for over twenty years that the resolution of rac-2-oxotricyclo[2.2.1.0$^{3,5}$]heptane-7-carboxylic acid can be effected with the aid of (S)-(-)-phenylethylamine, by preparation and multiple recrystallization of the phenethylammonium salt (Bindra, Grodski, Schaaf, Corey, J. Am. Chem. Soc. 1973, 95, 7522; Bartmann, Beck, Jähne, Lerch, Wess, Liebigs Ann. Chem. 1987, 321; CS 240,862). This process is very laborious and unacceptable on the industrial scale for economic reasons.

SUMMARY OF THE INVENTION

It has now been found that compounds of Formula I, described below, can be obtained in optically pure form from enantiomeric mixtures by enzymatic ester cleavage (i.e., hydrolysis).

The kinetic resolution is accomplished by subjecting the chiral, racemic carboxylic acid esters of Formula I to a lipase-, esterase- or protease-catalyzed steroselective hydrolysis in homogeneous or heterogeneous aqueous-organic media.

After the reaction has taken place, the unreacted ester and the acid formed—and thus the two enantiomers—may be separated.

The process according to the invention has the following advantages, in particular on the industrial scale, compared with the described resolution processes using optically pure amines:

- the enzymatic resolution or separation of enantiomers can be carried out economically, simply and rapidly: it does not require equimolar amounts of optically pure auxiliary agents or disproportionately large amounts of solvent and repeated, laborious, operating time equipment-intensive recrystallization can be dispensed with,
- after completion of the reaction, the separation of the products can be accomplished by simple measures, e.g. extraction.

The invention thus relates to a process for enzymatic resolution or separation of enantiomers from enantiomeric mixtures or racemic mixtures of compounds of Formula I

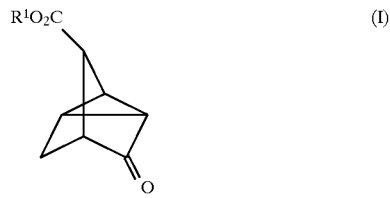

in which

R$^1$ is C$_1$–C$_{10}$-alkyl, C$_3$–C$_{10}$-cycloalkyl, C$_2$–C$_{10}$-alkenyl, C$_2$–C$_{10}$-alkynyl, C$_3$–C$_8$-cycloalkenyl, C$_5$–C$_{10}$-aryl or C$_5$–C$_{10}$-heteroaryl, wherein the alkyl, cycloalkyl, alkenyl, alkynyl and cycloalkenyl radicals may be monosubstituted, disubstituted or trisubstituted by F, Cl, Br, I, CN, CO$_2$(C$_1$–C$_4$)-alkyl, CONH$_2$, NR$^2$R$^3$, NO$_2$, (C$_1$–C$_4$)-alkoxy, O(CO)(C$_1$–C$_4$)alkoxy, SPh, SMe, SEt, SO$_2$Ph, SO$_2$(C$_1$–C$_4$)-alkyl, aryl or heteroaryl, alkyl and alkylene radicals having 3 to 10carbon atoms or alkynyl radicals having 4 to 10 carbon atoms, R$^2$ and R$^3$ are hydrogen, C$_1$–C$_6$-alkyl, C$_3$–C$_{10}$-cycloalkyl, C$_2$–C$_6$-alkenyl, C$_2$–C$_6$-alkynyl, phenyl, benzyl, benzoyl or amino protective groups, or in which R$^1$ is a radical of the formula II

R$^4$ and R$^5$ being hydrogen or (C$_1$–C$_6$)-alkyl and R$^4$ and R$^5$ together being an alkylene or an alkenylene radical or in which R$^1$ is a radical of the formula III

R$^6$, R$^7$ and R$^8$ being hydrogen, methyl or ethyl, or in which

R$^1$ is a radical of the formula IV

R$^9$ being hydrogen, (C$_1$–C$_4$)-alkyl or 2-oxotricyclo[2.2.1.0$^{3,5}$]heptane-7-carbonyl;

comprising the steps of forming a reaction mixture comprising:

enantiomeric mixtures or racemic mixtures of compounds of the above Formula I, lipases or esterases from porcine liver, porcine pancreas, bovine pancreas or from microorganisms such as Candida, Pseudomonas, Mucor, Rhizopus and Aspergillus, or proteases from Bacillus, water and, if desired, a cosolvent, reacting the reaction mixture, and separating the esters and acids so obtained.

The alkyl, alkenyl and alkynyl groups mentioned above and below can be either straight-chain or branched.

The term aryl may be understood as meaning aromatic moieties having 6 to 12 carbon atoms. Examples include phenyl or naphthyl moieties.

The term heteroaryl may be understood as meaning aromatic moieties having 3 to 7 carbon atoms, which contain at least one N, O or S atom. Examples include furyl or thienyl moieties.

The term amino protective group may be understood as meaning generally customary amino protective groups Examples include benzyloxycarbonyl (CBz=Z), butoxycarbonyl (BOC), allyloxycarbonyl (ALOC) or acetyl (Ac) groups.

DESCRIPTION OF THE PREFERRED EMBODIMENT(S)

Preferred racemic mixtures of compounds of Formula I employed are those in which $R^1$ is $C_1$–$C_{10}$-alkyl or $C_2$–$C_{10}$-alkenyl wherein the alkyl radicals may be substituted by F, Cl, Br, I, CN, $CO_2(C_1$–$C_4)$-alkyl, $NO_2$, $(C_1$–$C_4)$-alkoxy and $O(CO)(C_1$–$C_4)$-alkoxy, or in which $R^1$ is a radical of the formula II, $R^4$ and $R^5$ being hydrogen or methyl or in which $R^1$ is a radical of the formula III, $R^6$, $R^7$ and $R^8$ being hydrogen or ethyl, or in which $R^1$ is a radical of the formula IV, $R^9$ being hydrogen, $(C_1$–$C_4)$-alkyl or 2-oxotricyclo[$2.2.1.0^{3,5}$]heptane-7-carbonyl.

Particularly preferred compounds of the formula I are those in which $R^1$ is methyl or ethyl, or in which $R^1$ is a radical of the formula II, $R^4$ and $R^5$ being methyl, or in which $R^1$ is a radical of the formula III, $R^6$, $R^7$ and $R^8$ being hydrogen.

In the process according to the invention, a procedure is preferably used in which an ester of the formula I, for example the methyl ($R^1$=$CH_3$) or the vinyl ester ($R^1$=radical of the formula III where $R^6$=$R^7$=$R^8$=H) is treated with a lipase, esterase or protease in an aqueous solution and the mixture is stirred.

It can be advantageous to buffer the solution mentioned, e.g. with phthalate, phosphate or TRIS [=tris(hydroxymethyl)methylamine] buffer. The addition of buffer can be e.g. 0.01–1.0M; a convenient buffer range is pH 5–9.Furthermore, it can be advantageous to add an organic solvent to the reaction solution as a cosolvent. Suitable cosolvents are e.g. dimethoxyethane, acetone, THF, dioxane, hexane and tert-butyl methyl ether. The proportion of cosolvent in the solution is preferably 10 to 70%.

The enzymes preferably used are lipase SP 526 from *Candida antarctica* (commercially available from Novo Nordisk), porcine liver esterase (PLE, commercially available from Sigma Chemical Co.), lipase OF from *Candida cylindracea* (commercially available from Meito Sangyo Co.) and lipase P (or FP) from Pseudomonas spec. (commercially available from Amano Pharmaceuticals, Nagoya, Japan) and also alkalase (protease from *Bacillus licheniformis*, commercially available from Novo Nordisk). Alternatively, the enzymes mentioned may be prepared by prior art methods: methods for the culture—including recombinant DNA methods, if appropriate—of the microorganisms mentioned, and processes for the characterization, production and purification of the desired enzymes may be found in: Mikrobiologische und Biochemische Verfahrenstechnik [Microbiological and Biochemical Process Technology], A. Einsele et al., VCH Weinheim, 1985; Methods of Enzymatic Analysis, 3rd Edition, Vol. I–XII, H. -U. Bergmeyer, VCH Publishers, Weinheim 1986; Enzymes, 3rd Edition, M. Dixon, E. C. Webb, Academic Press, Inc. 1979.

Each of the enzymes mentioned may be employed in free or in immobilized form (Immobilized Biocatalysts, W. Hartmeier, Springer Verlag Berlin, 1988). The amount of enzyme is freely selected depending on the reaction rate or on the attempted reaction time (or the attempted conversion) and on the type of enzyme (e.g. free or immobilized) and can easily be determined by simple preliminary tests. The reaction mixture preferably contains 2–50% by weight of the compound of Formula I, particularly 5–20% of the compound of Formula I. The reaction temperature may be 10°–100° C., preferably 25°–80° C.

The conversion of rac-2-oxotricyclo[$2.2.1.0^{3,5}$]heptane-7-carboxylic acid (compound of Formula I where $R^1$=H) into the corresponding esters (compound of Formula I) may be accomplished using known chemical methods of esterification (Haslam, Tetrahedron 1980, 36, 2409; Höfle, Steglich, Vorbrüggen, Angew. Chem. 1978, 90, 602; Geckeler, Bayer, Chem. Ber. 1974, 107, 1271).

The products formed in the process or remaining may be separated in a simple manner, e.g. by precipitation, chromatographic methods or extraction, preferably extraction. The ester is obtained, for example, by simple extraction of the aqueous reaction mixture, e.g. with tert-butyl methyl ether; the acid formed by hydrolysis is obtained, for example, by concentration (e.g. freeze drying) of the water phase. Separation (and later reuse) of the enzyme are facilitated by immobilization.

By suitable conduct of the reaction, it is always at least possible to obtain one enantiomer in optically pure form. If it is attempted to obtain predominantly optically pure ester, the conversion should be above 50% based upon initial molar concentration of the compound of Formula I in the reaction mixture, and if predominantly optically pure acid is desired, the conversion should be less than 50% based upon initial molar concentration of the compound of Formula I in the reaction mixture.

Determination of the conversion in the enzymatic hydrolysis was carried out by HPLC (RP 8 LiChrosper® 60), and the determination of the optical purity was carried out by HPLC (Chiralcel® OD), GC (FS Lipodex®) and by comparison of the rotations. The following examples are intended to illustrate the present invention in greater detail, without limiting the scope of the invention.

Example 1

2.0 g (0.012 mol) of methyl rac-2-oxotricyclo[$2.2.1.0^{3,5}$]heptane-7-carboxylate (compound of the formula I where $R^1$=Me) are stirred in 50 ml of 0.1M potassium phosphate buffer, pH=7, at 23° C. with 300 mg of lipase SP 526 from *Candida antarctica* (Novo Nordisk) using a magnetic stirrer. The pH is kept constant with the aid of an autotitrator. After metering in approximately 14 ml of 0.5M NaOH, the reaction mixture is extracted with tert-butyl methyl ether. After drying with $Na_2SO_4$ and concentrating the organic phase, 0.81 g (0.0049 mol, 82%) of optically pure (HPLC [Chiracel OD, n-hexane+EtOH:100+1.1 ml/min, 210 nm]; 100% ee) methyl (1R,7R)-(+)-2-oxotricyclo[$2.2.1.0^{3,5}$]heptane-7-carboxylate is obtained.

Example 2

2.0 g (0.012 mol) of methyl rac-2-oxotricyclo[$2.2.1.0^{3,5}$]heptane-7-carboxylate (compound of the formula I where $R^1$=Me) are stirred in a mixture of 25 ml of 0.05M potassium phosphate buffer, pH=7, and 5 ml of acetone at 40° C. with 300 mg of lipase SP 526 from *Candida antarctica* (Novo Nordisk) using a magnetic stirrer. The pH is kept constant with the aid of an autotitrator. After metering in approximately 14.4 ml of 0.5M NaOH, the reaction mixture is extracted with tert-butyl methyl ether. After drying with Na$_2$SO$_4$ and concentrating the organic phase, 0.80 g (0.0048 mol, 80%) of optically pure (HPLC [Chiracel OD, n-hexane+EtOH:100+1.1 ml/min, 210 nm]; 100% ee) methyl (1R,7R)-(+)-2-oxotricyclo[2.2.1.0$^{3,5}$]heptane-7-carboxylate is obtained.

Example 3

2.0 g (0.011 mol) of ethyl rac-2-oxotricyclo[2.2.1.0$^{3,5}$]heptane-7-carboxylate (compound of the formula I where R$^1$=Et) are stirred in 25 ml of 0.1M potassium phosphate buffer, pH=7, at 50° C. with 300 mg of lipase SP 526 from *Candida antarctica* (Novo Nordisk) using a magnetic stirrer. The pH is kept constant with the aid of an autotitrator. After metering in approximately 12.0 ml of 0.5M NaOH, the reaction mixture is extracted with tert-butyl methyl ether. After drying with Na$_2$SO$_4$ and concentrating the organic phase, 0.89 g (0.005 mol, 90%) of ethyl (1R,7R)-(+)-2-oxotricyclo[2.2.1.0$^{3,5}$]heptane-7-carboxylate (HPLC [Chiracel OD, n-hexane+EtOH:100+1.1 ml/min, 210 nm]; 98% ee) is obtained.

Example 4

230.0 g (1.386 mol) of methyl rac-2-oxotricyclo[2.2.1.0$^{3,5}$]heptane-7-carboxylate (compound of the formula I where R$^1$=Me) are stirred in a mixture of 2.7 l of 0.05M potassium phosphate buffer, pH=7, and 300 ml of dimethoxyethane at 50° C. with 34.5 g of lipase SP 526 from *Candida antarctica* (Novo Nordisk). The pH is kept constant with the aid of an autotitrator. After metering in approximately 750 ml of 1.0M NaOH, the reaction mixture is extracted with tert-butyl methyl ether. After drying with Na$_2$SO$_4$ and concentrating the organic phase, 88.6 g (0.536 mol, 77.4%) of methyl (1R,7R)-(+)-2-oxotricyclo[2.2.1.0$^{3,5}$]heptane-7-carboxylate (GC [FS Lipodex E, 120° C., H$_2$, t$_{ret}$; 46.7 min]:>99% ee) are obtained.

Example 5

50 mg (0.28 mmol) of vinyl rac-2-oxotricyclo[2.2.1.0$^{3,5}$]heptane-7-carboxylate (compound of the formula I where R$^1$=radical of the formula III where R$^6$=R$^7$=R$^8$=H) are stirred in a mixture of 2 ml of 0.1M potassium phosphate buffer, pH=7, at 23° C. with 10 mg of lipase OF from *Candida cylindracea* (Meito Sangyo) using a magnetic stirrer. After 6 h, the reaction mixture is extracted with tert-butyl methyl ether. After drying with Na$_2$SO$_4$ and concentrating the organic phase, 15 mg (0.084 mmol, 60%) of vinyl (1R,7R)-(+)-2-oxotricyclo[2.2.1.0$^{3,5}$]heptane-7-carboxylate (HPLC [Chiracel OD, n-hexane+EtOH:100+1.1 ml/min, 210 nm]; 95% ee) are obtained.

What is claimed is:

1. A process for the enzymatic separation of enantiomers from enantiomeric mixtures or racemic mixtures of compounds of Formula I

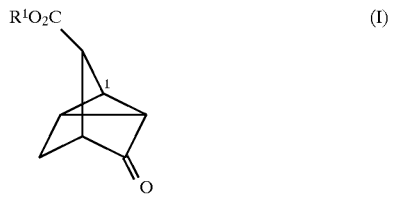

in which

R$^1$ is C$_1$–C$_{10}$-alkyl, C$_3$–C$_{10}$-cycloalkyl, C$_2$–C$_{10}$-alkenyl, C$_2$–C$_{10}$-alkynyl, C$_3$–C$_8$-cycloalkenyl, C$_5$–C$_{10}$-aryl or C$_5$–C$_{10}$-heteroaryl, wherein the alkyl, cycloalkyl, alkenyl, alkynyl and cycloalkenyl radicals may be monosubstituted, disubstituted or trisubstituted by F, Cl, Br, I, CN, CO$_2$(C$_1$–C$_4$)-alkyl, CONH$_2$, NR$^2$R$^3$, NO$_2$, (C$_1$–C$_4$)-alkoxy, O(CO)(C$_1$–C$_4$)-alkoxy, SPh, SMe, SEt, SO$_2$Ph, SO$_2$(C$_1$–C$_4$)-alkyl, aryl or heteroaryl, alkyl and alkylene radicals having 3 to 10 carbon atoms or alkynyl radicals having 4 to 10 carbon atoms, R$^2$ and R$^3$ are hydrogen, C$_1$–C$_6$-alkyl, C$_3$–C$_{10}$-cycloalkyl, C$_2$–C$_6$-alkenyl, C$_2$–C$_6$-alkynyl, phenyl, benzyl, benzoyl or amino protective groups, or in which R$^1$ is a radical of the formula II

R$^4$ and R$^5$ being hydrogen or (C$_1$–C$_6$)-alkyl or R$^4$ and R$^5$ together being an alkylene or an alkenylene radical or in which R$^1$ is a radical of the formula III

R$^6$, R$^7$ and R$^8$ being hydrogen, methyl or ethyl, or in which

R$^1$ is a radical of the formula IV

R$^9$ being hydrogen, (C$_1$–C$_4$)-alkyl or 2-oxotricyclo[2.2.1.0$^{3,5}$]heptane-7-carbonyl, which comprises the steps of forming a reaction mixture comprising enantiomeric mixtures or racemic mixtures of compounds of Formula I, lipase or esterase from Candida, and reacting the reaction mixture; and separating from one another the esters and acids so obtained.

2. The process as claimed in claim 1, wherein, of the substituents of Formula I, R$^1$ is C$_1$–C$_{10}$-alkyl or C$_2$–C$_{10}$-alkenyl, wherein the alkyl radicals may be substituted by F, Cl, Br, I, CN, CO$_2$(C$_1$–C$_4$)-alkyl, NO$_2$, (C$_1$–C$_4$)alkoxy and O(CO)(C$_1$–C$_4$)-alkoxy, or R$^1$ is a radical of the formula II, R$^4$ and R$^5$ being hydrogen or methyl or R$^1$ is a radical of the formula III, R$^6$, R$^7$ and R$^8$ being hydrogen or ethyl, or R$^1$ is a radical of the formula IV, R$^9$ being hydrogen, (C$_1$–C$_4$)-alkyl or 2-oxotricyclo[2.2.1.0$^{3,5}$]heptane-7-carbonyl.

3. The process as claimed in claim 1, wherein the reaction mixture additionally comprises a cosolvent.

4. The process as claimed in claim 2, wherein the reaction mixture additionally comprises a cosolvent.

5. The process as claimed in claim 1, wherein, of the substituents of Formula I, R$^1$ is methyl or ethyl, or R$^1$ is a radical of the formula II, R$^4$ and R$^5$ being methyl, or $R^1$ is a radical of the formula III, $R^6$, $R^7$ and $R^8$ being hydrogen.

6. The process as claimed in claim 2, wherein, of the substituents of the formula I, $R^1$ is methyl or ethyl, or $R^1$ is a radical of the formula II, $R^4$ and $R^5$ being methyl, or $R^1$ is a radical of the formula III, $R^6$, $R^7$ and $R^8$ being hydrogen.

7. The process as claimed in claim 1, wherein a lipase obtained from *Candida antarctica* is employed.

8. The process as claimed in claim 2, wherein a lipase obtained from *Candida antarctica* is employed.

9. The process as claimed in claim 5, wherein a lipase obtained from *Candida antarctica* is employed.

10. The process as claimed in claim 1, wherein the lipase or esterase, is employed in immobilized form.

11. The process as claimed in claim 2, wherein the lipase or esterase, is employed in immobilized form.

12. The process as claimed in claim 5, wherein the lipase or esterase, is employed in immobilized form.

13. The process as claimed in claim 6, wherein the lipase or esterase, is employed in immobilized form.

14. The process as claimed in claim 1, wherein the reaction mixture contains 2–50% ,by weight of the reaction mixture of the compound, of Formula I.

15. The process as claimed in claim 2, wherein the reaction mixture contains 2–50%, by weight of the reaction mixture, of the compound of Formula I.

16. The process as claimed in claim 5, wherein the reaction mixture contains 2–50%, by weight of the reaction mixture, of the compound of Formula I.

17. The process as claimed in claim 6, wherein the reaction mixture contains 2–50%, by weight of the reaction mixture, of the compound of Formula I.

18. The process as claimed in claim 1, wherein the reaction mixture additionally comprises a buffer.

* * * * *

UNITED STATES PATENT AND TRADEMARK OFFICE
CERTIFICATE OF CORRECTION

PATENT NO.   : 5,861,304
DATED        : January 19, 1999
INVENTOR(S)  : Wolfgang Holla et al.

It is certified that error appears in the above-identified patent and that said Letters Patent is hereby corrected as shown below:

Title page,
Item [54], should be replaced with the title, -- **PROCESS FOR THE RESOLUTION OF RAC-2-OXOTRICYCLO [2.2.1.0$^{3,5}$]HEPTANE-7-CARBOXYLIC ACID ESTERS USING LIPASE FROM *CANDIDA* --**

Column 6,
Line 41, "Candida" should read -- *Candida* --.
Line 43, insert a new line, -- water, --.

Column 7,
Line 18, after "esterase" delete -- , --.
Line 20, after "esterase" delete -- , --.

Column 8,
Line 2, after "esterase" delete -- , --.
Line 4, after "esterase" delete -- , --.
Line 6, change "2-50% , by" to -- 2-5%, by --; and
Line 7, replace "mixture of the compound," with -- mixture, of the compound --.

Signed and Sealed this

Ninth Day of July, 2002

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO. : 5,861,304
DATED : January 19, 1999
INVENTOR(S) : Wolfgang Holla et al.

Page 1 of 1

It is certified that error appears in the above-identified patent and that said Letters Patent is hereby corrected as shown below:

<u>Title page,</u>
Item [54], should be replaced with the title, -- **PROCESS FOR THE RESOLUTION OF RAC-2-OXOTRICYCLO [2.2.1.0$^{3,5}$]HEPTANE-7-CARBOXYLIC ACID ESTERS USING LIPASE FROM *CANDIDA* ** --

<u>Column 6,</u>
Line 41, "Candida" should read -- *Candida* --.
Line 43, insert a new line, -- water, --.

<u>Column 7,</u>
Line 18, after "esterase" delete -- , --.
Line 20, after "esterase" delete -- , --.

<u>Column 8,</u>
Line 2, after "esterase" delete -- , --.
Line 4, after "esterase" delete -- , --.
Line 6, change "2-50% , by" to -- 2-50%, by --; and
Line 7, replace "mixture of the compound," with -- mixture, of the compound --.

This certificate supersedes Certificate of Correction issued July 9, 2002.

Signed and Sealed this

Third Day of September, 2002

*Attest:*

*Attesting Officer*

JAMES E. ROGAN
*Director of the United States Patent and Trademark Office*